United States Patent
Winefordner et al.

(10) Patent No.: US 6,477,717 B1
(45) Date of Patent: Nov. 12, 2002

(54) SWIM MASK HAVING VIRTUAL BUCKLE PIVOT POINT

(75) Inventors: Carl Winefordner; Frank Hermansen, both of Laguna Beach, CA (US)

(73) Assignee: Q.D.S. Injection Molding, Inc., San Diego, CA (US)

(*) Notice: Subject to any disclaimer, the term of this patent is extended or adjusted under 35 U.S.C. 154(b) by 0 days.

(21) Appl. No.: 09/684,090

(22) Filed: Oct. 10, 2000

(51) Int. Cl.[7] .................................................. A61F 9/02
(52) U.S. Cl. .............................................. 2/428; 2/438
(58) Field of Search ........................... 2/428, 426, 452, 2/450, 453, 430, 909, 439, 438; 351/43

(56) References Cited

U.S. PATENT DOCUMENTS

| | | | | |
|---|---|---|---|---|
| 4,556,995 A | * | 12/1985 | Yamamoto | 2/439 |
| 4,649,577 A | * | 3/1987 | Wiedner | 2/436 |
| 4,688,337 A | * | 8/1987 | Dillner et al. | 24/616 |
| 4,795,385 A | * | 1/1989 | Matsuoka | 441/64 |
| 4,843,655 A | * | 7/1989 | Hegendorfer | 2/449 |
| 5,291,880 A | * | 3/1994 | Almovist et al. | 128/201.22 |
| 5,357,292 A | * | 10/1994 | Wiedner | 351/105 |
| 5,413,119 A | * | 5/1995 | Guerrant | 128/858 |
| 5,611,644 A | * | 3/1997 | Lutz | 405/186 |
| 5,652,954 A | * | 8/1997 | Paiement et al. | 2/10 |
| 5,657,493 A | * | 8/1997 | Ferrero et al. | 2/428 |
| 5,666,663 A | * | 9/1997 | Bolle | 2/10 |
| 5,860,168 A | * | 1/1999 | Winefordner et al. | 2/428 |
| 5,909,267 A | * | 6/1999 | Hall et al. | 351/120 |
| 5,956,778 A | * | 9/1999 | Godoy | 2/428 |
| 6,131,246 A | * | 10/2000 | Paulson et al. | 24/265 |
| 6,276,794 B1 | * | 8/2001 | Chiang | 351/43 |

FOREIGN PATENT DOCUMENTS

| | | | | |
|---|---|---|---|---|
| DE | | 512432 | * 9/1929 | 2/453 |

* cited by examiner

*Primary Examiner*—Gloria M. Hale
*Assistant Examiner*—Alissa L. Hoey
(74) *Attorney, Agent, or Firm*—Leonard Tachner

(57) ABSTRACT

A swim mask having a buckle that slides in a curved groove in the mask frame. The buckle has a virtual pivot point that is much farther forward than any prior art swivel mask buckle. In fact, the virtual pivot point could be infinitely in front of the mask if the groove were straight. The embodiment shown has a pivot point that is slightly in front of the mask lens. The preferred embodiment is also extremely simple to manufacture and assemble. It also has a means for being easily locked into any of several positions by the user. It is also aesthetically pleasing and allows easy strap adjustment. The preferred embodiment also has a means to attach to the mask frame such that it is extremely secure and cannot be accidentally detached and it also has only three components per buckle.

10 Claims, 7 Drawing Sheets

SWIM MASK HAVING VIRTUAL BUCKLE PIVOT POINT

BACKGROUND OF THE INVENTION

1. Field of the Invention

The present invention pertains generally to the field of swim masks and more particularly to swim masks having improved comfort as a result of a buckle with a pivot point in front of the mask lens.

2. Background Art

Swim mask buckles adjustably secure mask straps to mask frames. Prior art swim mask buckles are either fixed or swivel relative to the mask frame. Swivel swim mask buckles connect to the frame so that they can swivel about a pin through a limited angle. Both fixed and swivel buckles allow quick adjustment of the strap length. The main purpose of a swivel mask buckles is to allow the strap to move at an angle such that the mask is securely positioned. Secondarily, another purpose of the swivel is to allow the strap to be positioned above the user's ear which is more comfortable. In practice, the pivot point of prior art swivel buckles is so close to the user's ear that the strap cannot be positioned both above the user's ears and around the back of the user's head. Prior art swivel buckles do not allow the user to fixedly place the buckle in any of several swivelled positions so that the mask strap would remain in a more comfortable position during use. Moreover, prior art swivel buckles can often be accidentally dislodged from the mask frame because the means for attachment is unreliable. Additionally, prior art swivel buckles, including any attachment components or hardware, typically contain four or more components per buckle which causes higher manufacturing and assembly costs.

Because fixed buckles do not swivel, the strap must flex or bend in order to position the strap above the user's ears. In effect, the strap's pivot point is even closer to the user's ears than it is with prior art swivel buckles. Therefore, there are even more comfort problems for the user when using fixed buckles than when using prior art swivel buckles.

The ideal buckle would have a pivot point that is sufficiently far enough from the user's ears that the strap can be comfortably positioned both above the user's ears and still around the back area of the user's head. A pivot pin cannot be placed far enough forward to accomplish this because the pin would be so far forward that it would interfere with vision and/or with the mask lens and/or with the mask skirt. In fact, the ideal pivot position is in front of the mask lens. Therefore, the prior method of swiveling cannot be used to create the ideal buckle. The ideal buckle would also allow the user to fixedly place the buckle in any of several swivelled positions so that the mask strap would remain in the most comfortable position possible during use.

SUMMARY OF THE INVENTION

A swim mask having a buckle that slides in a curved groove in the mask frame. The buckle has a virtual pivot point that is much farther forward than any prior art swivel mask buckle. In fact, because of the unique adjustment in translation, the virtual pivot point could be infinitely in front of the mask if the groove were straight. The embodiment shown has a pivot point that is slightly in front of the mask lens. The preferred embodiment is also extremely simple to manufacture and assemble. It also has a means for being easily locked into any of several positions by the user. It is also aesthetically pleasing and allows easy strap adjustment. The preferred embodiment also has a means to attach to the mask frame such that it is extremely secure and cannot be accidentally detached and it also has only three components per buckle.

OBJECTS OF THE INVENTION

It is therefore a principal object of the present invention to provide a novel swim mask having a pair of buckles that result in a more comfortable strap configuration on a user.

It is another object of the invention to provide a swim mask having a buckle/frame interface which results in a virtual buckle pivot point in front of the mask.

It is still another object of the invention to provide a swim mask in which each buckle is moveable along a preferably curved elongated slot for extraordinary adjustability of the mask strap.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which.

DETAILED DESCRIPTION OF A PREFERRED EMBODIMENT

Figure 1:
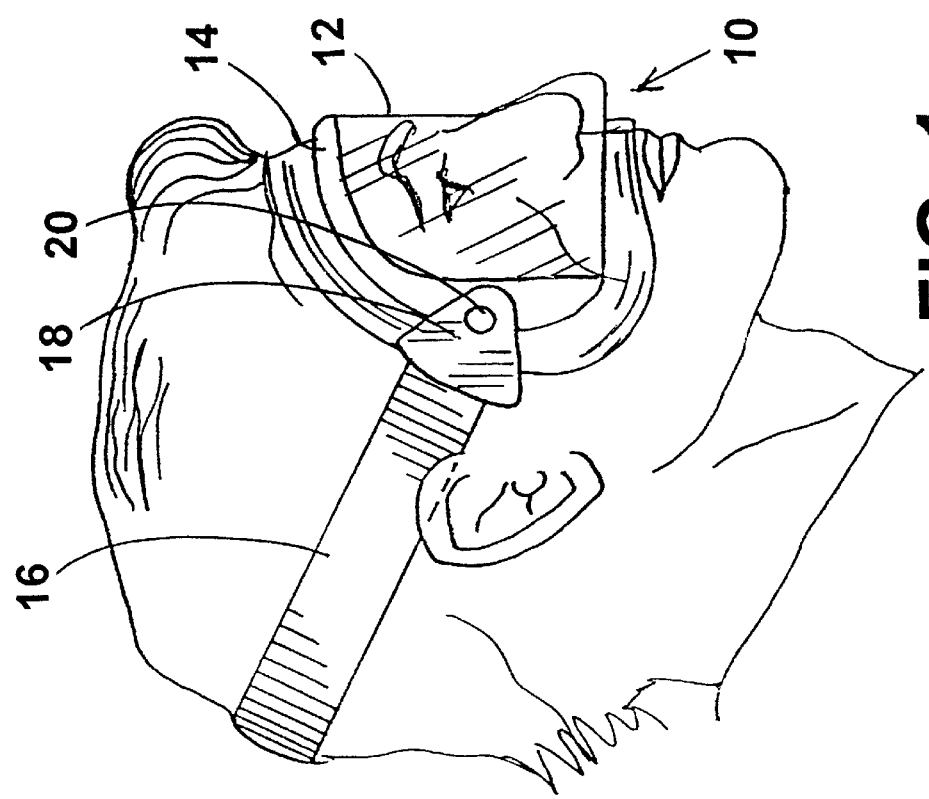
FIG. 1 is a side view of a prior art swivel buckle swim mask.

Referring to the prior art illustration of FIG. 1, it will be seen that a conventional swim mask 10 has a lens 12 in a frame 14 to which is attached a strap 16 by means of a buckle 18. Buckle 18 is attached to a swivel at pivot pin 20 which, as previously described, tends to position strap 16 so that it covers the upper portion of the user's ears.

Figure 2:
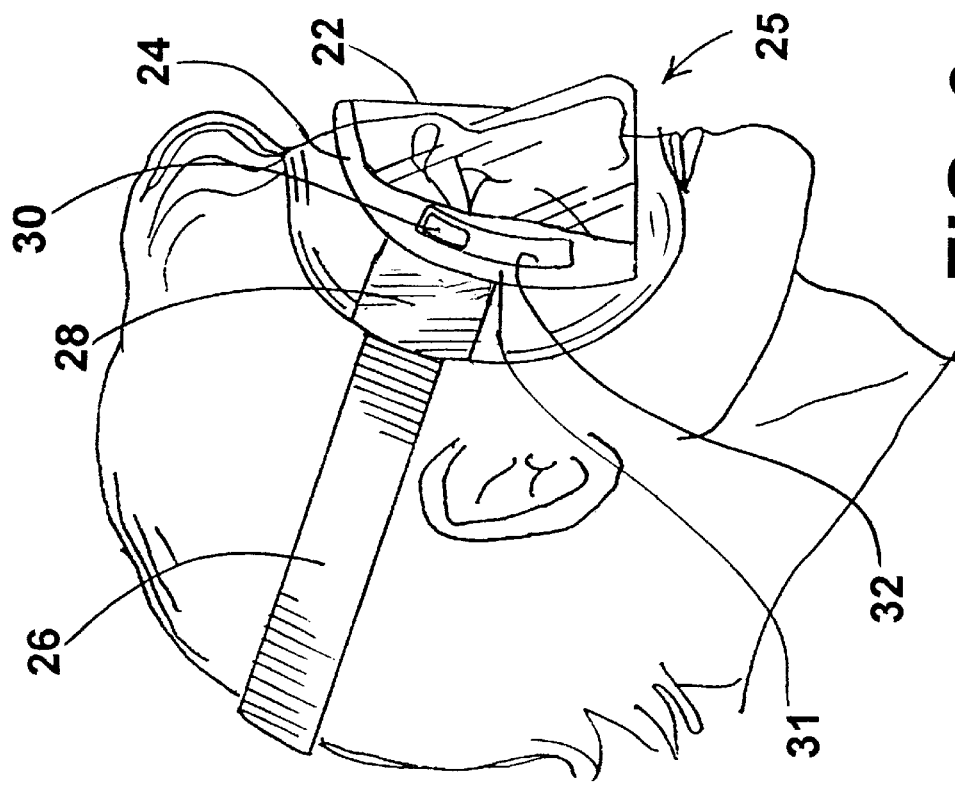
FIG. 2 is a view similar to FIG. 1, but of a swivel buckle according to a preferred embodiment of the invention.
Figure 3:
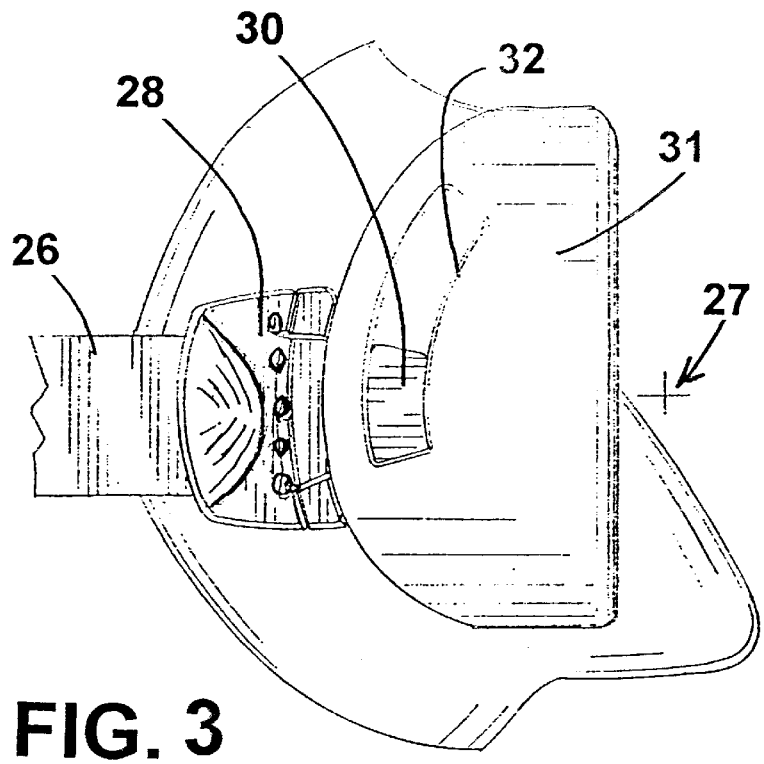
FIGS. 3 and 4 are enlarged side views of the inventive swim mask buckle shown in respective lower and upper portions.
Figure 4:
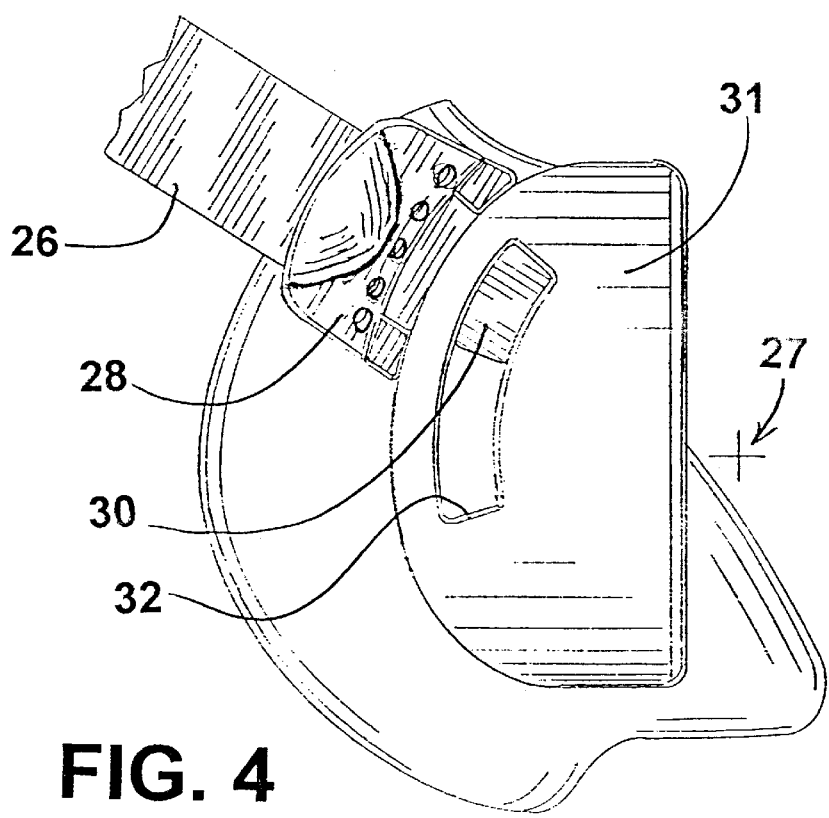

FIG. 2 illustrates the more adjustable and more comfortable strap position resulting from the novel buckle of the invention. The inventive dive mask 25 comprises a lens 22, a frame 24, a strap 26 and a buckle 28. It will be seen in FIGS. 2, 3 and 4 that buckle 28 connects to the frame side 31 so that a buckle rider 30 is positioned in a curved buckle slot 32 which produces a virtual pivot point 27.

Figure 5:
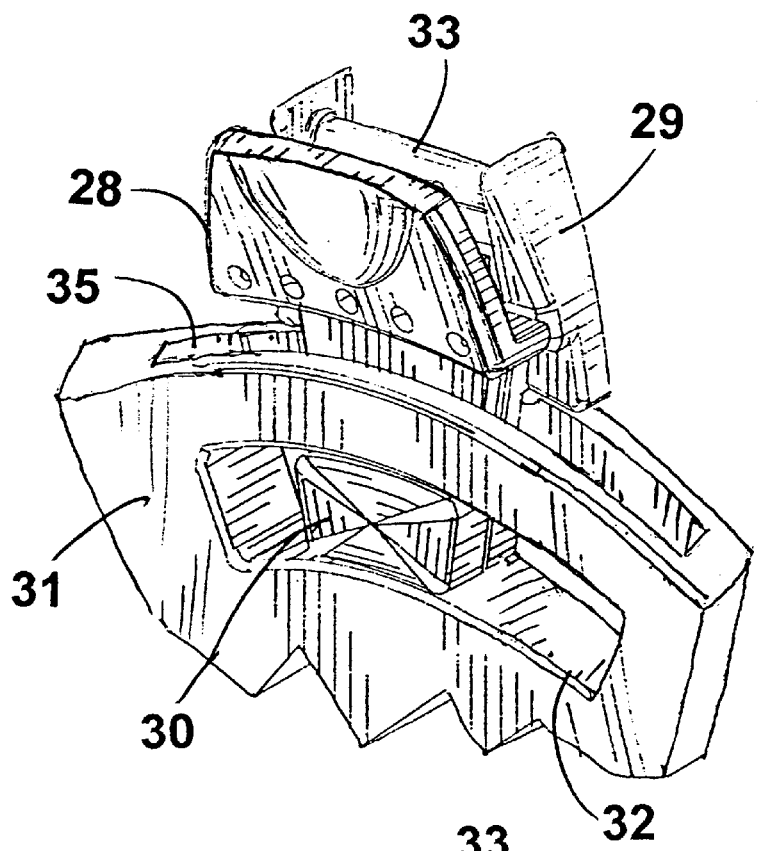
FIGS. 5 and 6 are further enlarged partial views showing the inventive buckle from outside and inside the mask frame, respectively.
Figure 6:
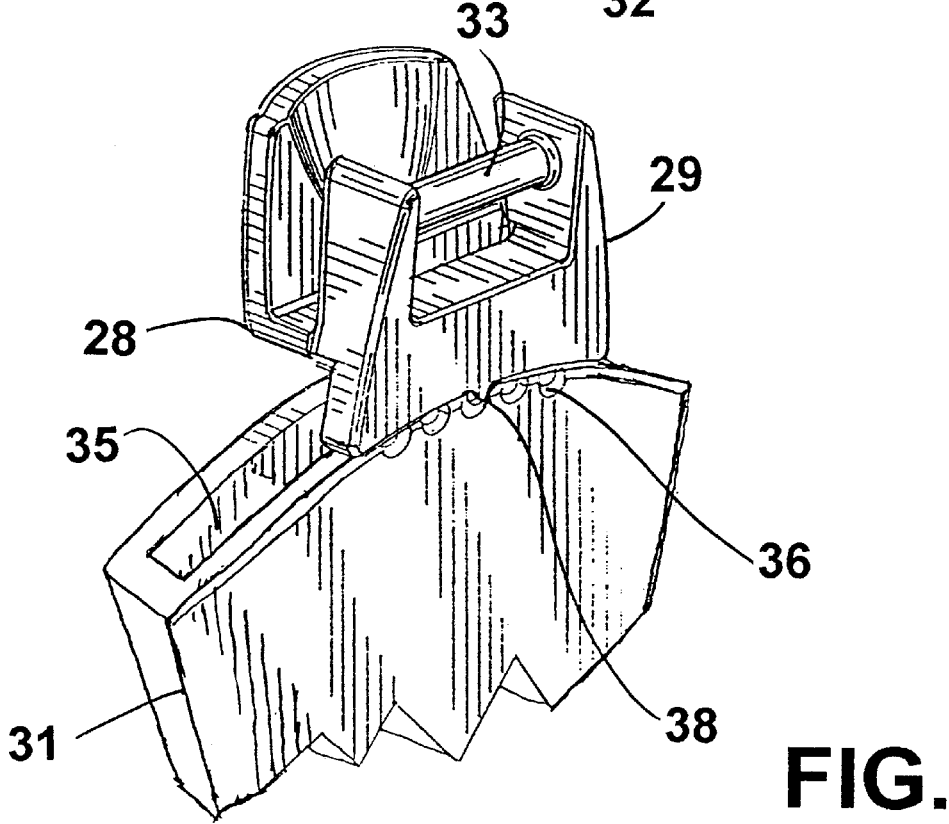
Figure 7:
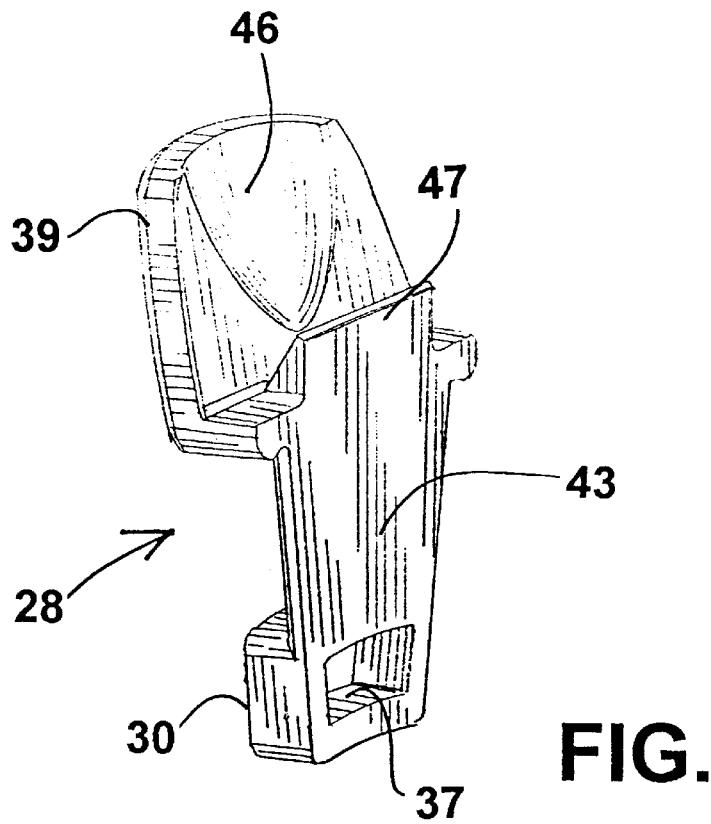
FIGS. 7 and are opposing side three-dimensional views of a top member of the inventive buckle.
Figure 8:
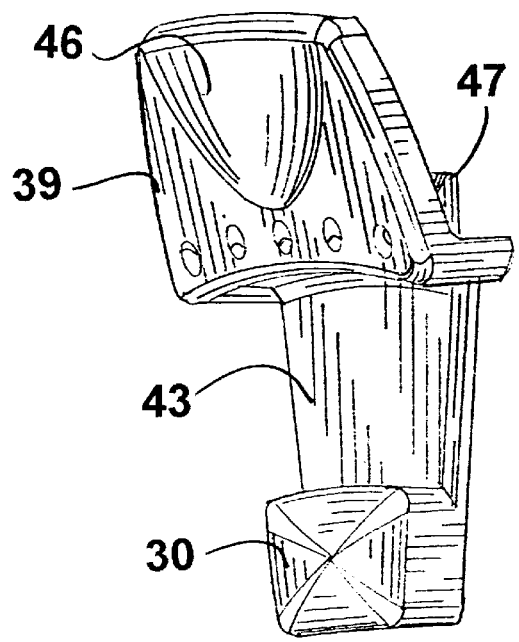
Figure 9:
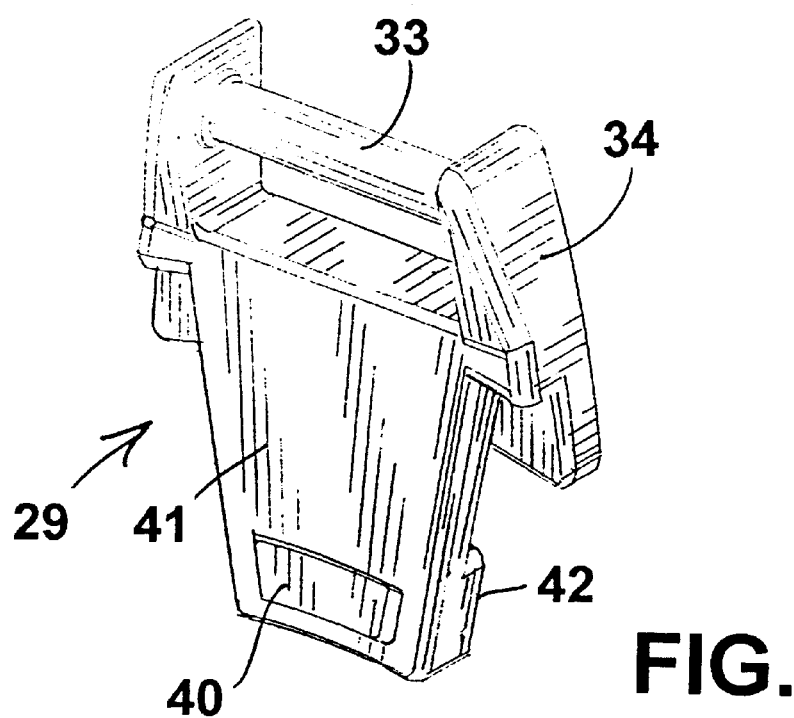
FIGS. 9 and 10 are opposing side three-dimensional views of a bottom member of the inventive buckle.
Figure 10:
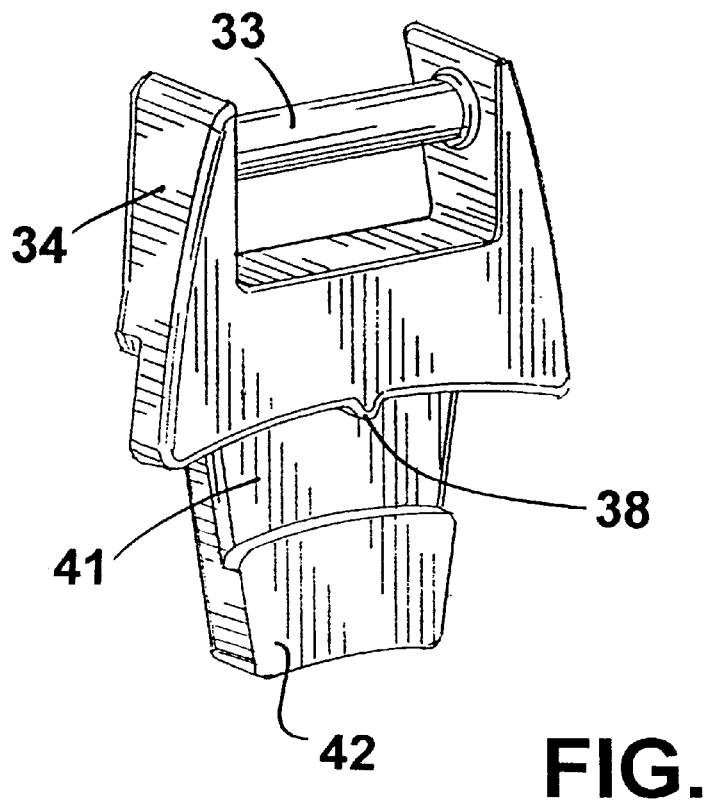

In FIGS. 5 and 6 it will be seen that the buckle is actually made up of two distinct parts, namely, a buckle top 28 and a buckle bottom 29. Top and bottom parts 28 and 29 are retained in a frame slot 35 in frame side 31. A plurality of depressions 36 along the top of frame side 31 cooperate with a tab 38 on buckle bottom part 29 to prevent inadvertent movement of the strap 26.

The individual buckle parts will now be described in conjunction with FIGS. 7–10. Top part 28 has a strap release 39 at the top of a flexible body 43. Body 43 terminates in buckle rider 30, the back of which is formed into a rectangular receptacle 37. The strap release 39 is provided with opposing finger depressions 46 and a strap stop 47.

Bottom part 29 provides a spool 33 supported by a pair of wing-like holders 34 which extend upwardly from a body 41. Body 41 terminates in a buckle lock 40 on one surface and a retainer 42 on the opposing surface.

Figure 11:
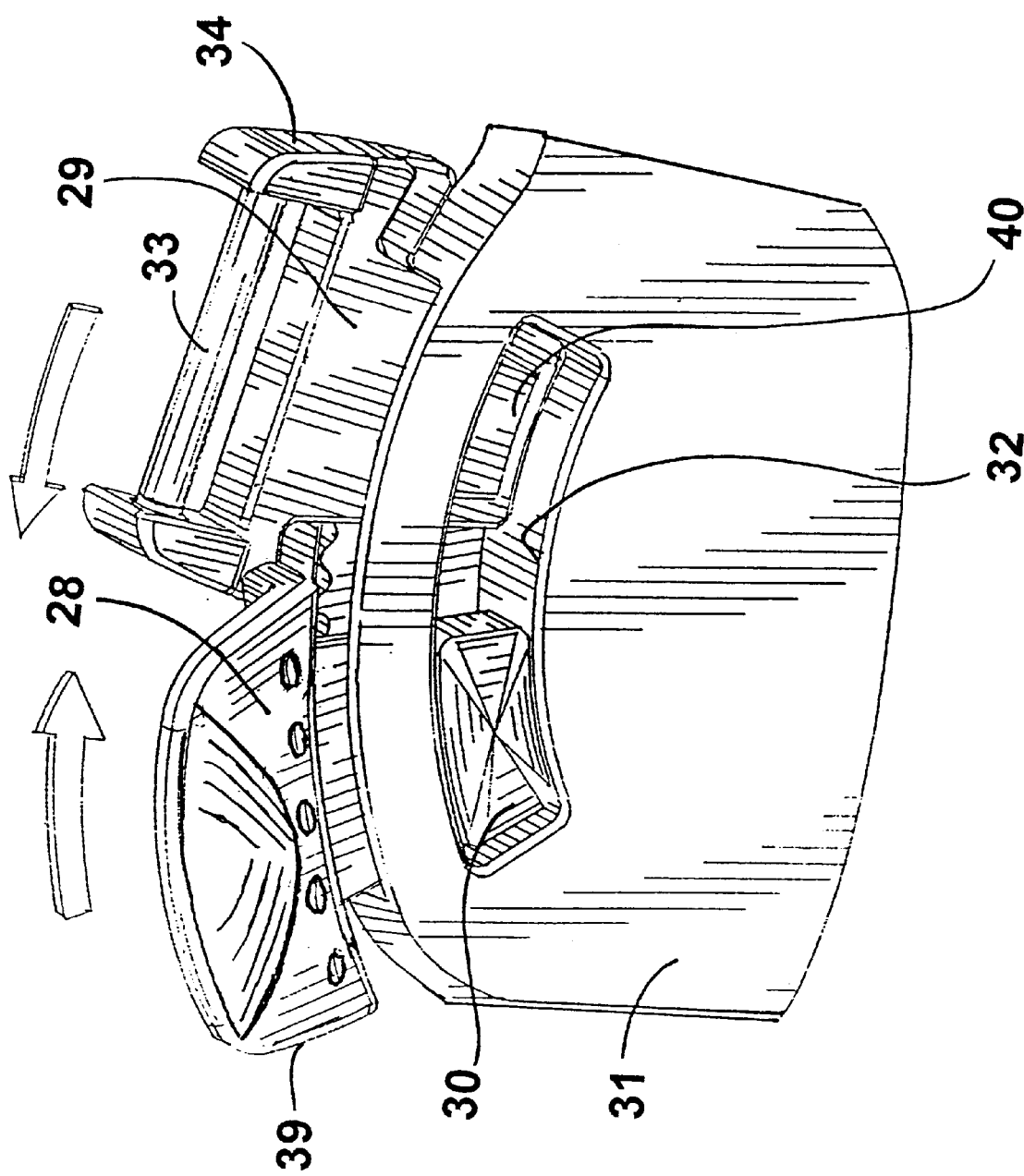
FIG. 11 is a three-dimensional view showing the assembly of top and bottom buckle members into the mask frame.

As shown in FIG. 11, the top and bottom parts are separately installed into frame side 31 via slot 35. They are then slide over one another until buckle lock 40 of part 29 enters receptacle 37 of part 28, thereby securing both parts together within curved buckle slot 32.

Figure 12:
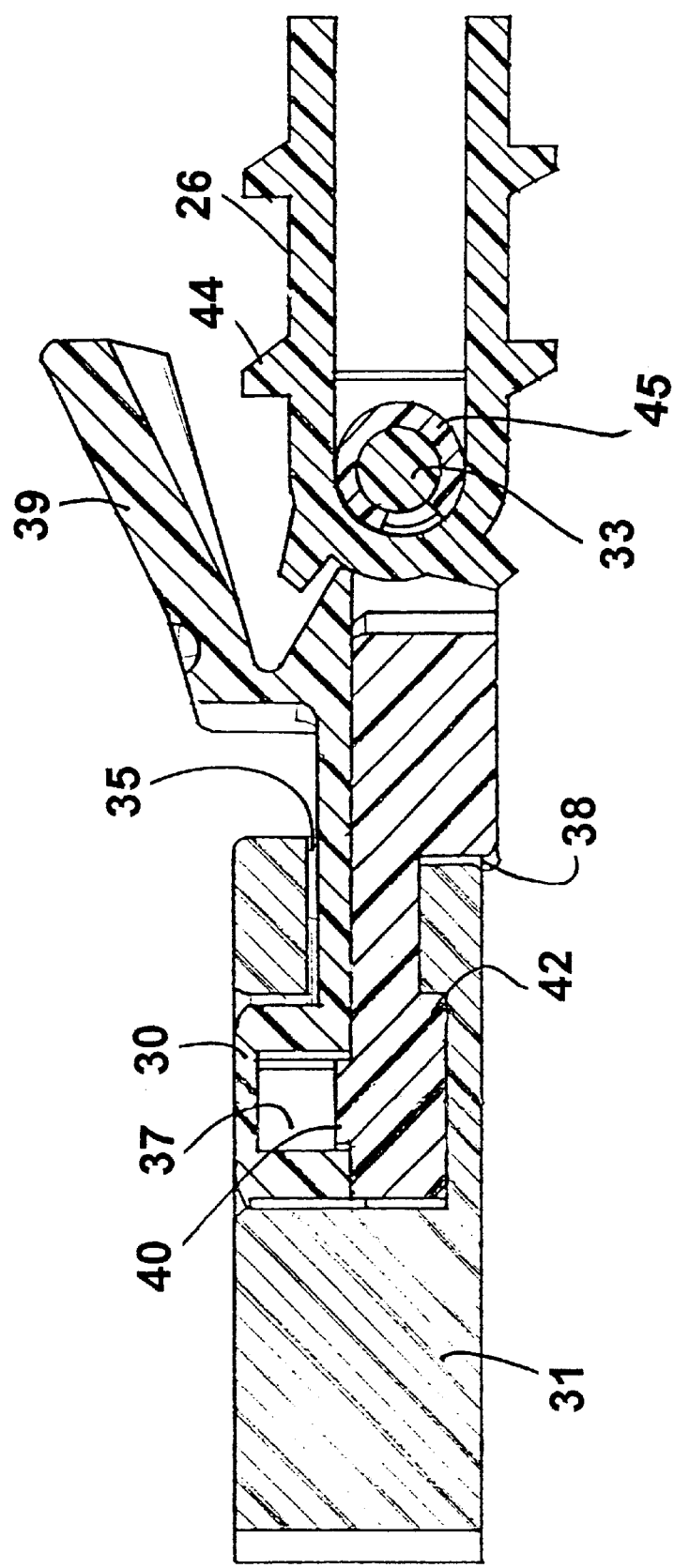
FIG. 12 is a cross-sectional view of the assembled buckle and frame with an attached strap.

The fully assemblied configuration of the preferred embodiment is illustrated in FIG. 12 with the inclusion of strap 26 and a roller 45 mounted around spool 33. Strap 26 is provided with teeth 44 which engage strap stop 47 when strap release 39 is relaxed as shown in FIG. 12.

Having disclosed a preferred embodiment of the invention in sufficient detail to enable a complete understanding of its structure and operation, it will be understood that variations are contemplated. Accordingly, the scope of protection hereof should be deemed to be limited only by the appended claims and their equivalents.

We claim:

1. A swim mask comprising a lens contained within a frame, a strap for securing the mask to a user's head and face and a pair of buckles for connecting the strap to the frame; the frame having elongated buckle slots for receiving said buckles in selectable slidable engagement for controlling the position of said strap on said user's head.

2. The swim mask recited in claim 1 wherein said elongated slots are arched to form a pivot point for said buckles.

3. The swim mask recited in claim 2 wherein said pivot point is a virtual pivot point positioned beyond said buckle.

4. The swim mask recited in claim 1 wherein said buckles each comprise a buckle rider, said rider being slidable engaged within a respective one of said elongated slots.

5. The swim mask recited in claim 4 wherein each of said buckles comprises a top part and a bottom part, one said parts having a spool for receiving said strap and the other of said parts having a strap stop device for releasably locking the strap to the buckle.

6. The swim mask recited in claim 5 wherein said top part and said bottom part of each said buckle comprise means for mechanically engaging one another within said elongated slot.

7. The swim mask recited in claim 1 wherein said frame comprises a plurality of spaced apart depressions adjacent each said buckle and wherein each said buckle comprises at least one tab extending into a selected one of said depressions for preventing inadvertent movement of each buckle within a corresponding slot of said frame.

8. The swim mask recited in claim 1 wherein each of said buckles comprises a top part and a bottom part, one said parts having a spool for receiving said strap and the other of said parts having a strap stop device for releasably locking the strap to the buckle.

9. The swim mask recited in claim 8 wherein said top part and said bottom part of each said buckle comprise means for mechanically engaging one another within said elongated slot.

10. The swim mask recited in claim 1 wherein said frame comprises a plurality of spaced apart depressions adjacent each said buckle and wherein each said buckle comprises at least one tab extending into a selected one of said depressions for preventing inadvertent movement of each buckle within a corresponding slot of said frame.

* * * * *